(12) United States Patent
Tanaka et al.

(10) Patent No.: US 7,176,347 B2
(45) Date of Patent: Feb. 13, 2007

(54) VEGETATIVE GROWTH SPECIFIC PROMOTER AND TRANSGENIC PLANT OBTAINED WITH THE SAME

(75) Inventors: Hiroshi Tanaka, Tsukuba (JP); Yasunori Ban, Tsukuba (JP); Toshiaki Kayano, Tsukuba (JP); Makoto Matsuoka, Nagoya (JP); Tomoaki Sakamoto, Tsukuba (JP)

(73) Assignee: National Institute of Agrobiological Sciences, Ibaraki (JP)

( * ) Notice: Subject to any disclaimer, the term of this patent is extended or adjusted under 35 U.S.C. 154(b) by 339 days.

(21) Appl. No.: 10/472,987

(22) PCT Filed: Mar. 27, 2001

(86) PCT No.: PCT/JP01/02512

§ 371 (c)(1),
(2), (4) Date: Sep. 26, 2003

(87) PCT Pub. No.: WO02/077248

PCT Pub. Date: Oct. 3, 2002

(65) Prior Publication Data

US 2004/0117876 A1 Jun. 17, 2004

(51) Int. Cl.
C12N 15/29 (2006.01)
C12N 15/82 (2006.01)
C12N 5/04 (2006.01)
A01H 5/00 (2006.01)
A01H 5/10 (2006.01)

(52) U.S. Cl. .................. 800/278; 536/24.1; 435/320.1; 435/419; 800/320; 800/306; 800/298; 800/290; 800/287

(58) Field of Classification Search ............... 536/23.1, 536/23.6, 24.1; 435/320.1, 419, 468; 800/278, 800/298, 290, 306, 320, 287
See application file for complete search history.

(56) References Cited

U.S. PATENT DOCUMENTS

2003/0172405 A1* 9/2003 Tanaka et al. .............. 800/287

FOREIGN PATENT DOCUMENTS

JP 10-248570 A 9/1998
WO WO 01/46434 A1 6/2001

OTHER PUBLICATIONS

The Merriam-Webster Online Dictionary (www.m-w.com/dictionary/indicated, 20.*
Kagaya et al (1995, Mol. Gen. Genet. 248 :668-674).*
Benfey et al (1990, Science 250:959-966).*
Benfey et al (1989, EMBO J, 8(8):2195-2202).*
Busch et al (1999, Science 285:585-587).*
Lohmann et al (2001, Cell 105 :793-803).*
Itoh, H. et al., "Cloning and functional analysis of two gibberellin 3β-hydroxylase genes that are differently expressed during the growth of rice", *PNAS* 98(15):8909-8914, 2001.
Itoh, H. et al., "The gene encoding tobacco gibberellin 3β-hydroxylase is expressed at the site of GA action during stem elongation and flower organ development", *The Plant Journal*, 20(1):15-24, 1999.
Ogawa, M. et al., "Rice gibberellin-insensitive gene homolog, *OsGAI*, encodes a nuclear-localized protein capable of gene activation at transcription level", *Gene*, 245(1):21-29, 2000.
Sakamoto, T. et al., "Expression of a gibberellin 2-oxidase gene around the shoot apex is related to phase transition in rice", *Plant Physiology*, 125:1508-1516, 2001.
Sakata, K. et al., "INE: a rice genome database with an integrated map view", *Nucleic Acids Research* 28(1):97-101, 2000.
Sakamoto et al., "Artificial Control of the Grass Type of *Oryza sativa* (rice) by Adjusting the Expression of Gibberellin Biosynthetic Enzyme Gene," *Chemistry and Biology* 38(2):131-139, (2000).
McElroy et al., "Isolation of an Efficient Actin Promoter for Use in Rice Transformation," *The Plant Cell* 2:163-171, (1990).

\* cited by examiner

*Primary Examiner*—Stuart F. Baum
(74) *Attorney, Agent, or Firm*—Jacqueline F. Mahoney; Perkins Coie LLP

(57) ABSTRACT

DNA having promoter activity for expressing an exogenous gene specifically in vegetative growth tissue (particularly, stems and/or leaves) is provided. The DNA is a rice OsGA3ox2 gene promoter which has a sequence indicated by SEQ ID NO. 1, or a portion of said sequence whose promoter activity is equivalent to that of said sequence indicated by SEQ ID No. 1. An expression vector containing an exogenous gene expressibly linked to the promoter is also provided. A plant cell transformed with the expression vector, a plant regenerated from the plant cell, a progeny of the plant, a propagator of the plant, and a seed obtained from the progeny are also provided. A method for introducing an exogenous gene into plants using an expression vector is also provided.

15 Claims, 6 Drawing Sheets

FIG. 2A

```
BamHI
ggatcccaccaatggcgacgcgccctctgctcctatcgatcccgacaacgcatccagaaggcgccggcgacacctcgccg        80
ccgatcgtccgcgccctagtcgccgccatctctcgatcatcccctgtccctctctctctctctctctctctccatttc        160
catcgccgcctacctccagacccaatgcatctctctctctctctattagtaaccattcatggatgatgatcatggc          240
tctctctctctctctgttaatttgtaatgtattagcaaccattcatggatgatgatcatggc                        320
                    PstI                              XbaI
ctctgtccctctgttttactcgtggctgcagactagtgctgtctttctcttgtttctctagaatctgtgtgctgt             400
tttctaaacaaattactgtttatatttgttttgttttgtagttgtaatataaggttagtcttcttagtaa                 480
atatattgaaaaagaagtagataacacggtttgaatcttgtacgtgctcgacaaattaggacgtaatc                   560
ctttcgtttcagattatataaatatttgacttagtaattaaatatttcataaattgtcttgagtttcaagttt              640
taataatatttataatattaattagtcaaactaaagtccttgatttgactaaagtcaaaacgtcttataacctgaaacgatgtag  720
ttttctataaattggtcaaacttaaagcagttgatttgactaaagtaaaatatcgaatgaaattcgacgtgtatgagaattat    800
tactgtatgggaactagcatgagatcttgctactgaaagtgagaatattggttcttcaaagcagacagaattaaaaaaaca      880
acggtaatcataattagaagtggctgcatgtgagaatattggttcttcaaagcagacagaattaaaaaaaca                960
ccacggcaacggagacgctacttcctgtgaaattcctatgttaattcctaatctgttttattgtaatgtgataat            1040
tataaaattactctgtcttcacattgtgatttactttactataacataacttaattgtatgaatatgtgtt                1120
tattaattggtggcagtgccactagccagccaggagtggtgatgagcatactagcatttgtgttgtagctaag              1200
ctggtggccttgtgctccacatcactcctgtcccaatcaccacacatttttcctctccaaatctattaatt                1280
```

FIG. 2B

```
aatgatccattcaattcttcatcactgattattcaccaattaattctctcttttttcttccactacgctccaaa    1360 acttctccctatatactctccctgtacttgtccagttcttacactcgtctcacttactactcattccactatt    1440 gtaaagtcatagaaaaaattatatagagagaaaaaattagtgtttgttattgtttgttactgctttctgccagacgagacga  1520 gcgagcgcgagtgtgttgtctctgttgtcatctcgtcgtcgtcggcgATGCCGACCCCGTCGCACTTGAAGAACCCGCTCT    1600
                                               M  P  T  P  S  H  L  K  N  P  L  C      12

GCTTCGACTTCCGGCGGGCCGAGGCGGGTGCCGGAGACGCACCGGTGCCGGACGACCACCCGGTGGTGGACGGC    1680
 F  D  F  R  A  A  R  R  V  P  E  T  H  A  W  P  G  L  D  D  D  H  P  V  V  D  G        38

GGCGGGCGGCGGCGAGGACGCGGTGCCGGTGGTGGACGTCAGGGCACGGCGGCGGCGCGCGTCGCGGGCGGC    1760
 G  G  G  G  E  D  A  V  P  V  V  D  V  R  A  G  D  A  A  A  R  V  A  A        65

GGAGCAGTGGGGCGCGTTCCTTCTCGTCGGGCACGGCGGTGCCGGCCGCCGCGCTCCTGAGCAGGGTCGCCC    1840
 E  Q  W  G  A  F  L  L  V  G  H  G  V  P  A  A  L  L  S  R  V  E  E  R  V  A  R        92

GCGTGTTCTCCCTGCCGGCGTCGGAGAAGATGCGCGCCGTCCGCGGCGAGCCCGGCGGCTACGGCTCGCCGCCC    1920
 V  F  S  L  P  A  S  E  K  M  R  A  V  R  G  P  E  P  C  G  Y  G  S  P  P             118

ATCTCCTCCTTCTTCTCCAAGCTCATGTGGTCCGAGGGCTACACCTTCTCCCCTTCCTCCCTGCGCTCCGAGCTCCGCCG    2000
 I  S  S  F  F  S  K  L  M  W  S  E  G  Y  T  F  S  P  S  S  L  R  S  E  L  R  R       145
                                                                    SacI

CCTCTGGCCCAAGTCCGGCGGCGACTACCTCCTCTTCTGtatatacatatatactctcccatgcattccatgc    2080
 L  W  P  K  S  G  G  D  Y  L  L  F  C                                                  158
```

FIG.2C

```
acatacactctacgtatatatctctacgtattgatctacgtataatacgcagTGACGTGATG    2160
                                                    D  V  M      161

GAGGAGTTTCACAAGGAGATGCGGCGGCTAGCCGACGAGTTGCTGAGGTTGTTCTTGAGGCGCTAGGGCTCACCGGCGA    2240
 E  E  F  H  K  E  M  R  R  R  L  A  D  E  L  L  R  L  F  L  R  A  L  G  L  T  G  E    188

GGAGGTCGCCGGAGTCGAGGCGGAGAGGAGGATCGGGCGAGACGGTGCACCTCAACTGGTACCACGTTAACCCGAGGT    2320
 E  V  A  G  V  E  A  E  R  R  I  G  E  R  M  T  A  T  V  H  L  N  W  Y  P  R  C    215

GCCCGGAGCCGCGGCGGCGAGCGCTGGGGCTCATCGCCACACGACTCGGGCTTCTTCGTCTCCAGAGCCTCGTC    2400
 P  E  P  R  R  A  L  G  L  I  A  H  T  D  S  G  F  F  F  V  L  Q  S  L  V    241

CCGGGG    2406
 P  G     243
Sma I
```

VEGETATIVE GROWTH SPECIFIC PROMOTER AND TRANSGENIC PLANT OBTAINED WITH THE SAME

TECHNICAL FIELD

The present invention relates to breeding of useful plants using a plant gene promoter. More particularly, the present invention relates to breeding of useful plants using a promoter gene of the 3β hydroxylase 2 gene (hereinafter referred to as OsGA3ox2) of rice.

BACKGROUND ART

Dwarfism, which is caused by artificial modification of plant shape (particularly, suppression of elongation growth), is a considerably important target for breeding of crops. Dwarfism is an abnormality of growth which is caused as a result of a mutation in a gene involved in the regulation of normal elongation growth. The elongation growth of plants is achieved by repetition of cell division and cell elongation, which are regulated by complex influences due to various factors, such as external environment factors (e.g., temperature, light, and the like), and internal environment factors (e.g., plant hormones, and the like). Therefore, it is inferred that a variety of genes are involved in dwarfism, such as genes directly involved in synthesis or reception of plant hormones, genes involved in expression regulation thereof, and the like. Among other things, an abnormality in the biosynthesis pathway of gibberellin is well known as a cause of dwarfism.

Gibberellin biosynthesis in higher plants includes three stages, which are catalyzed by enzymes existing in plastids, endoplasmic reticular membranes, and cytoplasm, respectively. In the third stage, in which GA12 aldehyde and subsequent substances are processed, there are two pathways of early-13 hydroxylation hydroxylase and a non-hydroxylase. In both pathways, gibberellin is physiologically activated by its carbon at position 3 being hydroxylated by 3β hydroxylase, and subsequently, is inactivated by its carbon at position 2 being hydroxylated by 2β hydroxylase.

In rice, it is known that at least two 3β hydroxylase genes exist (OsGA3ox1 and OsGA3ox2) in rice. One of them, OsGA3ox2, was demonstrated to correspond to the D18 (dy) gene locus which has been long known as a rice dwarfism gene. A 2β hydroxylase gene of rice, OsGA2ox1, was isolated as a novel gene belonging to a group of 2-oxoglutaric acid-dependent enzyme genes. Attempts have been made to suppress the elongation growth of plants by regulating these enzymes directly involved in conversion of active and inactive gibberellins (Kagaku-to-Seibutsu [Chemistry and Biology], Vol. 38, 2000, pp. 131–139). Among them, an attempt was made in which by regulating the expression level of a 2β hydroxylase gene in transformed plants, the content of active endogenous gibberellin is changed so as to obtain plants having a desired height. However, when OsGA2ox1 is forcedly expressed throughout a whole plant using an actin promoter which is a conventional constitutive promoter, gibberellin is unavoidably metabolized in reproductive organs as well as stems and leaves. As a result, the content of endogenous gibberellin is radically reduced to an extent that shows superdwarfism. In such a transformant, reproductive organs which require a large amount of gibberellin are also prevented from normally growing. Therefore, when a transformed plant having dwarfism is developed by overexpression of the 2β hydroxylase gene, it is necessary to suppress the influence on reproductive organs by utilizing a promoter working specifically in vegetative growth tissue.

For tobacco, the localization of plant expression tissue of a gene encoding 3β hydroxylase (Nty gene) has been investigated (see Plant Journal (1999) 20(1), 15–24). In this research, the promoter region of the Nty gene was linked to the GUS gene, and how the gene was expressed in various tissues in plants was observed. As a result, it was found that expression of the GUS gene linked to the promoter region of the Nty gene was limited to the site of action of gibberellin, including vegetative growth tissue. This research only found a relationship between the expression of the gene encoding 3β hydroxylase and the action of gibberellin. Therefore, no vegetative tissue specific promoter, which can be practically used, has been discovered.

Therefore, if a promoter for expression in vegetative growth tissue, whose activity is high and which can be practically used, is obtained from rice genes, it can contribute much to breeding of useful plants including rice and the like.

DISCLOSURE OF THE INVENTION

The present invention relates to plant breeding using genetic engineering techniques. An object of the present invention is to provide a plant gene promoter having a high level of activity in vegetative growth tissue (particularly, stems and/or leaves), an expression vector containing the gene, and a method using the gene.

The present inventors found that the rice 3β hydroxylase 2 (OsGA3ox2) gene has a high level of promoter activity in vegetative growth tissue (particularly, stems and/or leaves), and completed the present invention based on this finding.

The present invention provides DNA having promoter activity for expressing an exogenous gene specifically in plant vegetative growth tissue. This DNA has the sequence indicated by SEQ ID NO. 1 (FIGS. 2A to 2C) or a portion of the sequence whose promoter activity is equivalent to sequence indicated by SEQ ID NO. 1. The sequence indicated by SEQ ID NO. 1 contains a 5' upstream region of the rice OsGA3ox2 structural gene, a first exon, a first intron, and a portion of a second exon. In one embodiment of the present invention, this DNA is hybridizable to the sequence indicated by SEQ ID NO. 1 or a sequence having a portion of said sequence under stringent conditions.

The present invention also provides an expression vector for expressing an exogenous gene specifically in vegetative growth tissue (particularly, stems and/or leaves). This expression vector contains a rice OsGA3ox2 gene promoter, which has the sequence indicated by SEQ ID NO. 1 or a portion of the sequence whose promoter activity is equivalent to that of the sequence indicated by SEQ ID NO. 1, and further, an exogenous gene expressibly linked to this promoter. In one embodiment, the exogenous gene may have a function of suppressing elongation of stems and/or leaves. In another embodiment, the exogenous gene is a gene encoding 2β hydroxylase. The present invention also provides a plant cell (which may be a monocotyledonous plant cell or dicotyledonous plant cell) transformed with the expression vector, a plant regenerated from this plant cell, a progeny and a propagator of this plant, and a seed obtained from a progeny of this plant.

The present invention also provides a method for introducing an exogenous gene, which is intended to be expressed specifically in plant vegetative growth tissue, into plants. This method comprises the steps of: transforming a plant cell with the above-described expression vector; and obtaining a plant by redifferentiation of this transformed plant cell.

The above-described exogenous gene may be a gene having a function of suppressing elongation of stems and/or leaves. By applying such a gene in the above-described method, dwarf plants can be produced. In the above-described method, the plant cell may be either a monocotyledonous plant cell or a dicotyledonous plant cell.

BRIEF DESCRIPTION OF THE DRAWINGS

FIGS. 2A to 2C are diagrams showing the sequence of a region containing the 5' nontranslational sequence of OsGA3ox2, a first exon, a first intron, and a portion of a second exon (SEQ ID NO:1). In FIGS. 2A to 2C, bases indicated by capital letters indicate exon sites (position 1567 to 2039 and 2151 to 2406), and an encoded amino acid sequence is shown under the base sequence. In FIGS. 2A to 2C, restriction enzyme recognition sites are also shown.

BEST MODE FOR CARRYING OUT THE INVENTION

Figure 1:
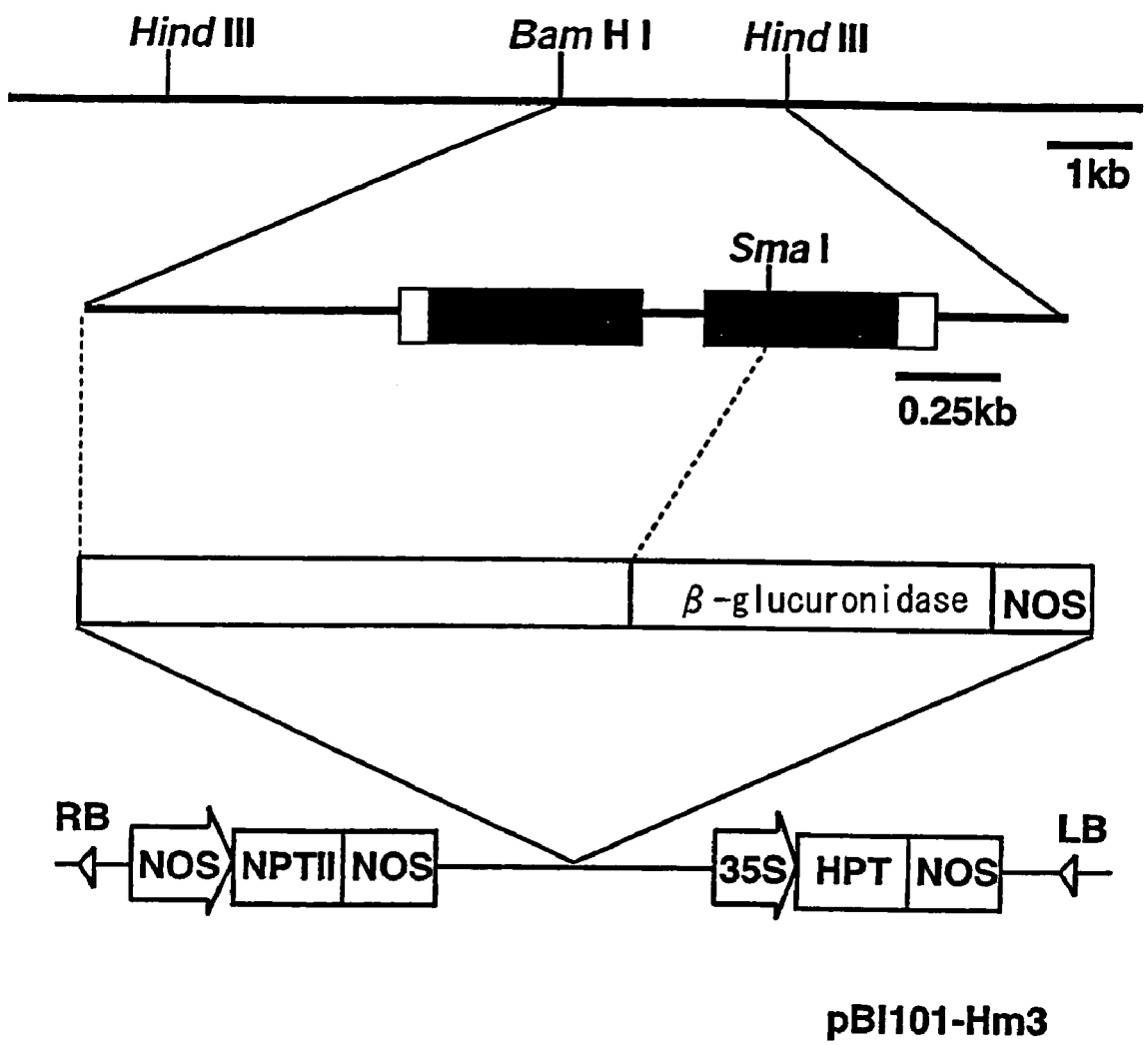
FIG. 1 is a schematic diagram showing production of an expression vector pBI101-Hm3 used in an example of the present invention.

Hereinafter, the present invention will be described in more detail.

(Isolation of a Rice OsGA3ox2 Gene Promoter)

A rice OsGA3ox2 gene promoter can be obtained by screening a rice genomic library. A rice genomic DNA library (Rice Genomic Library) commercially available from CLONTECH Laboratories Inc., Palo Alto, Calif. can be used.

As a probe for screening, rice OsGA3ox2 cDNA which was isolated by the the present inventors can be used.

Initially, *E. coli* is infected with a rice genomic gene library which is produced using phage λ, followed by formation of plaques. These plaques are transferred to a membrane, such as nitrocellulose or the like, using a commonly used method, followed by hybridization with labeled screening probes. After hybridization, the membrane is washed, followed by autoradiography. DNA is prepared from a phage for which hybridization is confirmed.

The prepared phage DNA is digested with a combination of appropriate restriction enzymes, and the resultant fragments are separated by agarose gel electrophoresis. The separated DNA fragments are transferred to a nylon membrane, followed by hybridization with the above-described screening probe. Screening is performed based on signal intensity and a band pattern difference.

It is believed that a clone having the most intense signal contains the OsGA3ox2 gene, while clones having weaker signals contain a gene similar to, but not, OsGA3ox2. Further, by comparing band patterns, it is possible to identify a clone lacking a part of the gene. Furthermore, by producing a physical map of each clone based on a band pattern thereof, it is possible to specify a clone having a 5' region of about 1.6 Kbp in length upstream of a structural gene, which is inferred to include a promoter.

In the above-described manner, the complete OsGA3ox2 genomic gene can be isolated.

By comparing the base sequence of the OsGA3ox2 genomic gene with the base sequence of OsGA3ox2 cDNA, a promoter region can be specified. If the genomic gene has an intron, the promoter sequence may contain not only the 5' region upstream of the structural gene but also a region, such as a first intron or the like. This promoter sequence is preferably a sequence indicated by SEQ ID NO. 1 (see FIGS. 2A to 2C). The sequence indicated by SEQ ID NO. 1 contains a 5' region upstream of the rice OsGA3ox2 structural gene, a first exon, a first intron, and a portion of a second exon.

(Specification of an Active Portion of a Promoter by Measuring GUS Activity)

When the promoter region of the OsGA3ox2 gene is specified, the sequence thereof can be excised and integrated into a plant expression vector. In order to assess the activity of the integrated promoter, aplasmid can be produced, in which a reporter gene, such as a gene encoding an appropriate enzyme, is linked downstream of the promoter. This plasmid is introduced into plant cells, and expression of the gene is observed by, for example, measuring enzyme activity. When plants are used as hosts, for example, it is usual to use a plasmid, such as pBI221 or the like, to carry out measurement with expression of β-glucuronidase (GUS) or the like as an indicator. This measurement method using GUS expression can be herein used.

GUS activity can be measured in accordance with a procedure described in, for example, Syokubutsu-saibo-kogaku [Plant Cell Engineering], Vol. 4, No. 4, pp. 281–286 (1992); Syokubutsu-saibo-kogaku [Plant Cell Engineering], Vol. 5, No. 5, pp. 407–413 (1992); and Plant Mole. Biol. Reporter 5(4) 387–405 (1987). The measurement method is not so limited. Briefly, tissue or a section of a plant is immersed and incubated in histochemical substrate solution containing 1 mM 5-bromo-4-chloro-3-indolyl-β-D-glucuronide (X-Gluc), 7% (v/v) methanol, and 50 mM sodium phosphate buffer solution (pH 7.0) at a temperature and a time which are appropriate for progression of a reaction (e.g., 37° C. and 30 minutes to 4 hours when a fusion gene of GUS and a CaMV promoter or the like is introduced). In order to prevent browning and GUS inactivation, a reducing agent, such as dithiothreitol (DTT) or the like, may be added. For example, 2 mM DTT may be added immediately after sectioning (when sections are prepared) in the stage of embedding the section in agar; in the stage of slicing the section; or in deaerating the section under reduced pressure. 5 mM DTT may also be added in a GUS reaction at 37° C. Thereafter, the reaction is arrested by addition of ethanol, followed by decoloration. The resultant tissue or section is observed under a microscope or a stereomicroscope.

Various deletion mutants in the promoter region of the OsGA3ox2 gene (e.g., the promoter region of the OsGA3ox2 gene partially deleted into various lengths from the 5' upstream side) are fused with the GUS gene in a plasmid. This plasmid is used to measure promoter activity. As a result, a portion or the like essential for the promoter activity can be specified. A method for specifying such an active portion is known to those skilled in the art. Therefore, for example, a sequence, which is obtained by removing a sequence unnecessary for the promoter region of the OsGA3ox2 gene and has the same activity as that of the promoter of the OsGA3ox2 gene, is within the scope of the present invention.

Once the promoter region of the OsGA3ox2 gene and the active portion thereof are specified, the sequence thereof can be modified so as to improve the promoter activity and change the specificity for tissue in which expression is performed. For example, a sequence, which is obtained by partially modifying the promoter region of the OsGA3ox2 gene or an active portion thereof and has activity equivalent to that before modification, is within the scope of the present invention.

The promoter region having the sequence of SEQ ID NO. 1 (FIGS. 2A to 2C) expresses activity specifically in vegetative growth tissue. Therefore, the term "equivalent" in promoter activity indicates that the intensity of activity is substantially the same as the intensity of the activity of at least a promoter region as a reference, and meanwhile, the specificity of activity is substantially the same as the specificity of the activity of the promoter region as a reference. It should be noted that the term "equivalent" is not intended to exclude the case where the intensity and specificity of activity are clearly higher than those of a promoter region as a reference. "Having promoter activity equivalent to that of the sequence of SEQ ID NO. 1" indicates that, for example, when the GUS gene is expressed in protoplasts under conditions described below, the GUS activity is at least about 50%, preferably at least about 70%, and more preferably at least about 90% of the GUS activity of the sequence of SEQ ID NO. 1 and is expressed specifically in vegetative growth tissue.

The scope of the present invention may encompass a sequence hybridizable to the promoter region of the OsGA3ox2 gene or the active portion thereof under stringent conditions. As used herein, "stringent hybridization conditions" or "stringency" refers to conditions in a range from about 5° C. to about 20° C. or 25° C. below the melting temperature ($T_m$) of the target sequence and a probe with exact or nearly exact complementarity to the target. As used herein, the melting temperature is the temperature at which a population of double-stranded nucleic acid molecules becomes half-dissociated into single strands. Methods for calculating the $T_m$ of nucleic acids are well known in the art (see, e.g., Berger and Kimmel, 1987, Methods In Enzymology, Vol. 152: Guide To Molecular Cloning Techniques, San Diego: Academic Press, Inc., and Sambrook et al., (1989) Molecular Cloning: A Laboratory Manual, 2nd Ed., Vols. 1–3, Cold Spring Harbor Laboratory, hereinafter referred to as "Sambrook", both incorporated herein by reference). As indicated by standard references, a simple estimate of the $T_m$ value may be calculated by the equation: $T_m=81.5+0.41$ (% G+C), when a nucleic acid is in aqueous solution at 1 M NaCl (see e.g., Anderson and Young, Quantitative Filter Hybridization in NUCLEIC ACID HYBRIDIZATION (1985)). Other references include more sophisticated computations which take structural as well as sequence characteristics into account for the calculation of $T_m$. The melting temperature of a hybrid (and thus the conditions for stringent hybridization) is affected by various factors, such as the length and nature (DNA, RNA, base composition) of the probe and the nature of the target (DNA, RNA, base composition, present in solution or immobilized, and the like), and the concentration of salts and other components (e.g., the presence or absence of formamide, dextran sulfate, polyethylene glycol). The effects of these factors are well known and are discussed in standard references in the art, see e.g., Sambrook, supra, and Ausubel et al., Current Protocols in Molecular Biology, Greene Publishing and Wiley-Interscience, New York (1997). Typically, stringent hybridization conditions are salt concentrations less than about 1.0 M sodium ion, typically about 0.01 to 1.0 M sodium ion at pH 7.0 to 8.3, and temperatures at least about 30° C. for short probes (e.g., 10 to 50 nucleotides) and at least about 60° C. for long probes (e.g., greater than 50 nucleotides). As noted, stringent conditions may also be achieved with the addition of destabilizing agents such as formamide, in which case lower temperatures may be employed. For example, when two polynucleotides are specifically hybridized with each other under stringent hybridization conditions, they are identified as having substantial sequence identity. As used herein, the terms "substantial identity", "substantial sequence identity" or "substantial similarity" refers to the degree of sequence similarity between two polynucleotides in the context of nucleic acid. Alternatively, substantial sequence identity is described as percent identity between two nucleotide (or polypeptide) sequences. When two sequences have at least about 60%, preferably at least about 70% identity, at least about 80% identity, or at least about 90% identity, at least about 95% or 98%–100% identity, they are considered to be substantially identical to each other. Another degree of sequence identity (e.g., "substantially" less than) can be characterized by hybridization under different stringency conditions. The percent identity of sequences (nucleotides or amino acids) is typically calculated by determining optimal alignment of two sequences, and then comparing the two sequences. For example, exogenous transcripts employed in protein expression may be described as having a particular percent identity or similarity when compared with a reference sequence (e.g., a corresponding endogenous sequence). Optimal alignment of sequences may be conducted by the homology alignment algorithm of Needleman and Wunsch (1970) J. Mol. Biol. 48:443, by the search for similarity methods of Pearson and Lipman (1988) Proc. Natl. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by inspection by the local homology algorithm of Smith and Waterman (1981) Adv. Appl. Math. 2:482. The best alignment (i.e., the highest percent identity is obtained) is selected from those obtained by various methods. Typically, these algorithms compare two sequences over a "comparison window" (usually at least 18 nucleotides long) to identify and compare local regions of sequence similarity, and therefore, enables small additions or deletions (i.e., gaps). Additions and deletions typically have a length of 20 percent or less as compared to reference sequences without an addition or a deletion. It is sometimes preferable to describe sequence identity between two sequences by referencing a particular length or region (e.g., two sequences may be described as having at least 95% identity over a length of at least 500 base pairs). Usually, the length is at least about 50, 100, 200, 300, 400, or 500 base pairs, amino acids, or other residues. A percent of sequence identity is calculated by comparing two sequences optimally aligned over a comparison region where the number of sites at which the same nucleic acid bases (e.g., A, T, C, G or U) occur in both sequences is determined to obtain the number of matching sites, and comparing it with the total number (or percent) of bases of a reference sequence or a comparison region. Another algorithm suitable for measurement of sequence similarity is a BLAST algorithm, which is described in Altschul (1990) J. Mol. Biol. 215:403–410; and Shpaer (1996) Genomics 38:179–191. Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Extension of the word hits in each direction are halted when: the cumulative alignment score falls off by the unknown quantity X from its maximum achieved value; the cumulative score goes to zero or below, due to the accumulation of one or more negative-scoring residue alignments; or the extension reaches to the end of either sequence. The BLAST algorithm parameters W, T, and X determine the sensitivity and speed of the alignment. The BLAST program uses as defaults a wordlength (W) of 11, the BLOSUM62 scoring matrix (see Henikoff (1992) Proc. Natl. Acad. Sci. USA 89:10915–10919) alignments (B) of 50, expectation (E) of 10, M=5, N=−4, and a comparison of both strands. The term BLAST refers to a BLAST algorithm for statistically analyzing similarity between two sequences. See Karlin (1993) Proc. Natl. Acd. Sci. USA 90:5873–5787. One measure of similarity provided by the BLAST algorithm is the smallest sum probability (P(N)), which provides an indication of the probability by which a match between two nucleotide or amino acid sequences would occur by chance. Alternatively, another indication that two nucleic acid sequences are similar is that the polypeptide encoded by the first nucleic acid is immunologically cross reactive with the polypeptide encoded by the second nucleic acid.

As used herein, "specifically" expressed in vegetative growth tissue indicates that an intended gene product is expressed in vegetative growth tissue more than in at least another tissue or organ of the same plant. "Vegetative growth tissue" refers to tissue which is not directly involved in sexual reproduction of plants, including all tissues constructing vegetative organs, such as roots, stems, and leaves. "Specifically" expressed in vegetative growth tissue indicates that, for example, a gene product is expressed in at least one of stem and leaf more than flower organs on any other sites of the same plant. The specificity of such expression can be assessed by producing transformed plants under conditions similar to those described in the examples hereinbelow.

(Construction and Use of an Expression Cassette and a Recombinant Plasmid)

A sequence having the promoter region of the OsGA3ox2 gene whose activity has been confirmed or an active portion thereof can be incorporated into an appropriate plant expression vector. To the 3' end of the sequence incorporated in the plant expression vector is linked an appropriate linker sequence (e.g., a linker having a multiple cloning site), so that an expression cassette suitable for a plant host can be produced. Therefore, as used herein, "site for inserting an exogenous gene" refers to a site contained in a linker or a sequence having an action similar to that of the linker. This expression cassette may optionally contain another regulatory element. For example, a terminator sequence may be contained for the purpose of improving expression efficiency or the like. This terminator sequence can be linked to a promoter sequence via the above-described linker sequence having a multiple cloning site. The expression cassette may further contain a selectable marker gene appropriate for particular host organisms used.

An exogenous gene, which is intended to be expressed, is expressibly linked to a 3' downstream of a promoter of the above-described plant expression cassette, such as a multiple cloning site, resulting in a recombinant plasmid. As used herein, "exogenous gene" refers to any gene which is an endogenous gene of rice or other plants other than the OsGA3ox2 gene, or a foreign gene with respect to plants and whose gene product expression is desirable to vegetative growth tissue (particularly, stems and/or leaves).

With the resultant recombinant plasmid, plant cells can be transformed. Transformation of plant cells can be conducted by any method known to those skilled in the art, such as a method using *Agrobacterium*, electroporation into protoplasts, or the like. For example, plant cell protoplasts can be prepared in accordance with a method described in Kyozuka et al., Mol. Gen. Genet. 206:408–413 (1987). An example of a transformation method using *Agrobacterium*, which is preferable for monocotyledonous plants, is a method developed by the present inventors, which is described in PCT/JP/03920. With this method, monocotyledonous plants can also be transformed more quickly and efficiently. Transformation methods for plants are not so limited.

Transformed plant cells can be redifferentiated by a commonly used method into transformed plant tissue, and further, a whole plant. In production of recombinant plasmids for transformation, the OsGA3ox2 gene promoter can be incorporated into a binary vector which is expressible in both bacterium and plant hosts. Such a binary vector is well known to those skilled in the art. For example, when pBI vectors or the like (including an *Agrobacterium* expression system) are used, a system for infecting plants with microorganisms can be utilized. By using an appropriate recombinant plasmid, an exogenous gene of interest can be introduced into any transformable plant, including monocotyledonous plants (e.g., rice and the like) and dicotyledonous plants (e.g., tobacco and the like).

"Plant cell" may be any plant cell. A plant cell may be in any form of a culture cell, a culture tissue, a culture organ, or a whole plant, preferably a culture cell, a culture tissue, or a culture organ, and more preferably a culture cell. A plant species which can be used in a production method of the present invention may be any plant species into which a gene can be introduced.

Examples of plant species which can be used in production of the present invention include plants in the families of Solanaceae, Poaeae, Brassicaceae, Rosaceae, Leguminosae, Curcurbitaceae, Lamiaceae, Liliaceae, Chenopodiaceae and Umbelliferae.

Examples of plants in the Solanaceae family include plants in the *Nicotiana, Solanum, Datura, Lycopersion* and *Petunia* genera. Specific examples include tobacco, eggplant, potato, tomato, chili pepper, and petunia.

Examples of plants in the Poaeae family include plants in the *Oryza, Hordenum, Secale, Saccharum, Echinochloa* and *Zea* genera. Specific examples include rice, barley, rye, *Echinochloa crus-galli*, sorghum, and maize.

Examples of plants in the Brassicaceae family include plants in the *Raphanus, Brassica, Arabidopsis, Wasabia*, and *Capsella* genera. Specific examples include Japanese white radish, rapeseed, *Arabidopsis thaliana*, Japanese horseradish, and *Capsella bursa-pastoris*.

Examples of plants in the Rosaceae family include plants in the *Orunus, Malus, Pynus, Fragaria,* and *Rosa* genera.Specific examples include plum, peach, apple, pear, Dutch strawberry, and rose.

Examples of plants in the Leguminosae family include plants in the *Glycine, Vigna, Phaseolus, Pisum, Vicia, Arachis, Trifolium, Alphalfa,* and *Medicago* genera. Specific examples include soybean, adzuki bean, kidney bean, pea, fava bean, peanut, clover, and bur clover.

Examples of plants in the Cucurbitaceae family include plants in the *Luffa, Cucurbita,* and *Cucumis* genera. Specific examples include gourd, pumpkin, cucumber, and melon.

Examples of plants in the Lamiaceae family include plants in the *Lavandula, Mentha,* and *Perilla* genera. Specific examples include lavender, peppermint, and beefsteak plant.

Examples of plants in the Liliaceae family include plants in the *Allium, Lilium,* and *Tulipa* genera. Specific examples include onion, garlic, lily, and tulip.

Examples of plants in the Chenopodiaceae family include plants in the *Spinacia* genera. A specific example is spinach.

Examples of plants in the Umbelliferae family include plants in the *Angelica, Daucus, Cryptotaenia,* and *Apitum* genera. Specific examples include Japanese udo, carrot, honewort, and celery.

"Plants" on which a promoter of the present invention acts include any plant into which a gene can be introduced. "Plants" includes monocotyledonous and dicotyledonous plants. Such plants include any useful plants, particularly crop plants, vegetable plants, and flowering plants of garden varieties. Preferable plants include, but are not limited to, rice, maize, sorghum, barley, wheat, rye, *Echinochloa crusgalli*, foxtail millet, asparagus, potato, Japanese white radish, soybean, pea, rapeseed, spinach, tomato, and petunia. The most preferable plant to which the present invention is applied is rice, particularly Japonica rice.

As described above, the OsGA3ox2 gene promoter can be expressed specifically in vegetative growth tissue (particularly, stems and/or leaves). Therefore, by using a gene having a function of suppressing elongation of stems and/or leaves as an exogenous gene, dwarf plants can be produced. As used herein, a "gene having a function of inhibiting elongation of stems and/or leaves" refers to a gene whose gene product can suppress elongation of stems and/or leaves, for example, genes encoding enzymes involved in a gibberellin degradation system (particularly, 2β hydroxylase which hydroxylate carbon at position 2 of the gibberellin backbone to convert activated gibberellin (GA1 and GA4), where carbon at position 3 of the gibberellin backbone is activated by 3β hydroxylase, to inactivated gibberellin (GA8 and GA34), enzymes involved in expansion and elongation of cell walls, for example, various cell wall polysaccharide synthesis enzymes (e.g., glucanase, cellulose, and hemicellulase), and the like; and genes having a function of suppressing elongation of stems and/or leaves by themselves, for example, antisense RNA for endogenous genes expressed in elongation of vegetative growth tissue (particularly, stems and/or leaves), such as genes involved in a gibberellin synthesis system (e.g., *Arabidopsis thaliana* GA4 gene) and genes encoding enzymes involved in a gibberellin synthesis system such as 20 oxidase and 3β hydroxylase, and ribozymes which can degrade such endogenous genes. Methods for screening of dwarf plants and breeding of plants are well known to those skilled in the art. The above-described genes involved in the signal transduction system for gibberellin, genes involved in the brassinolide synthesis system and a signal transduction system thereof, and the like may be involved in dwarfism of plants.

The above-described production of transformed plants can be utilized so as to confer traits other than dwarfism to plants. For example, by using an exogenous gene encoding a toxic protein, it is possible to control insects eating stems and leaves, and the like. The present invention encompasses production of any useful plant using gene expression specific to vegetative growth tissue (particularly, stems and/or leaves). A gene expressed by the promoter of the present invention may also include a gene encoding a protein degrading a chemical substance. An illustrative example of such a protein is a protein that degrades herbicide. By using an exogenous gene encoding a protein that degrades herbicide, a desired plant can be screed for by applying herbicide.

An action of the promoter of the present invention may be inherited by the primary generation of transformed plants as well as subsequent generations of the plants. The action of the promoter may be exhibited in the primary generation of transformed plants and subsequent generations of the plants, propagators thereof (e.g., pollen), and seed produced from the propagators. Inheritance of an introduced promoter gene into subsequent generations can be confirmed by Southern analysis using a sequence of the promoter of the present invention as a probe.

According to the present invention, use of a practical promoter from a rice gene, which has a high level of activity in vegetative growth tissue (particularly, stems and/or leaves) is provided. Therefore, the present invention may be utilized in not only breeding of rice but also breeding of other various plants.

EXAMPLES

The present invention will be described in detail by ways of examples. These examples are not intended to limit the present invention. Materials, reagents, and the like used in the examples are available from commercial sources unless otherwise mentioned.

Example 1

Expression of the GUS Gene by the Rice OsGA3ox2 Promoter

1. Isolation of a Rice OsGA3ox2 Genomic Gene: Screening of a Genomic Library (Plant Materials)

Rice seeds (*Oryza sativa*, Japonica cultivars: "Nipponbare", "Dontokoi", "Koshihikari" and the like) were sterilized in 1% sodium hypochlorite for 1 hour and thoroughly rinsed in sterile distilled water. The seeds were germinated on soil and grown in a greenhouse.

(Procedure)

PCR was performed using the rice genomic DNA as a template and degenerate primers (a 5' primer: 5'-GTNGT-NAARGTNGGNGARRT-3' (SEQ ID NO. 2); and a 3' primer: 5'-AYYTARTCRTTGGANGTNAC-3' (SEQ ID NO. 3)) designed from the conserved region among the reported GA 3β hydroxylase sequences. A putative amino acid sequence primer of the resultant products was similar to a corresponding region in the reported GA 3β hydroxylase. A 210 bp DNA fragment was obtained which corresponds to the size expected from the reported GA 3β hydroxylase sequence. This PCR product was used as a probe for screening of a rice genomic library. Several clones were isolated and divided into two groups based on a restriction map of each genome clone. Finally, a clone of each group was sequenced and was designated OsGA3ox1 or OsGA3ox2 (OsGA3ox1 and OsGA3ox2 refer to *Oryza sativa* GA 3β hydroxylase-1 and *Oryza sativa* GA 3β hydroxylase-2, respectively). Thus, clones OsGA3ox1 and OsGA3ox2 containing the whole GA 3β hydroxylase gene were isolated. OsGA3ox1 shared a sequence in common with the fragment which the present inventions used as a probe. OsGA3ox2 contained a different sequence from the fragment in a corresponding region. A full-length cDNA clone encoding GA 3β hydroxylase was obtained by reverse transcription PCR (RT-PCR) using total RNA isolated from rice stem apices and flower organs which had not flowered using a specific primer. For RNA gel blotting analysis and DNA gel blotting analysis, a BssHII-PvuII (519 bp) fragment derived from OsGA3ox2 total cDNA and a KpnI-PvuII (310 bp) fragment derived from OsGA3ox1 (gene specific probes) were used. When each specific probe was used as a probe for genomic Southern hybridization, cross hybridization was not detected (data not shown). Each cDNA (OsGA3ox1 or OsGA3ox2) contained an open reading frame encoding a polypeptide of 379 amino acids or 370 amino acids (data not shown). The genomic OsGA3ox2 contained an intron having a short size (110 bp). This intron was located at the same site as that of GA 3β hydroxylase previously reported for dicotyledonous plants. The other clone OsGA3ox1 includes two introns. One intron was located at the same site as that of the OsGA3ox2. The one intron had substantially the same size as that of the other intron (110 bp). The other intron was located at a site to which a cofactor binds to (e.g., a cofactor 2-oxoglutaric acid (400 bp) binding site (data not shown)). Putative amino acid sequences of both of the clones had a high level of similarity to other GA 3β hydroxylases and the highest level of similarity to each other (56.6% identity and 88.2% similarity).

2. Production of a Recombinant Plasmid Having an OsGA3ox2 Gene Promoter

FIG. 1 shows production of a vector having a rice OsGA3ox2 gene promoter.

In order to obtain fragments which may contain a 5' nontranslational region of the rice OsGA3ox2 gene, the clone obtained in Section 1 was cloned with BamHI and HindIII, and about 2.5 Kbp fragments were recovered by agarose electrophoresis. A function of the promoter of the OsGA3ox2 gene was confirmed using a plant cell expression vector pBI101 (CLONTECH Laboratories Inc., Palo Alto, Calif.). This vector had a nopaline synthase promoter (NOS-Pro), a neomycin phosphotransferase II coding region (NP-TII (KON R)) for conferring kanamycin resistance, a terminator for nopaline synthase (NOS-T), a β-glucuronidase (GUS) coding region, and a terminator for nopaline synthase (NOS-T) in this order. This pBI101 was digested with HindIII and SmaI. The OsGA3ox2 gene fragments were digested with SmaI in order to insert them into the expression vector. The resultant fragment contained a sequence of position 1-2406 of the insertion sequence in the clone (SEQ ID NO:1), a 5' nontranslational sequence, a first exon, a first intron, and a portion of a second exon (FIGS. 2A to 2C). The 5' terminus of the fragment is a BamHI site and the 3' terminus thereof is a SmaI site. This fragment was linked to the expression vector which had been restriction digested as described above, resulting in pBI101-Hm3 containing fusion with a GUS reporter gene. In this expression vector, the hygromycin phosphotransferase (HPT) gene (located between the cauliflower mosaic virus 35S (35S) and a terminator for the nopaline synthase gene (Tnos)) were also inserted downstream of the GUS coding region in order to confer hygromycin resistance.

3. Transformation of Rice Seeds and Expression of the GUS Gene

Seeds of Nipponbare, which is a representative cultivar of rice, were immersed in 70% ethanol for 10 sec, where the seeds remained intact after removal of their chaffs. The seeds were washed with water, followed by immersion in 0.1% Tween20 and 2.5% sodium hypochlorite (NaClO) aqueous solution for 30 min, for sterilization. After thorough washing with water, the rice was subjected to the following sterile manipulations.

(Preculture)

The seeds were disseminated on 2,4-D containing N6D medium(30 g/l sucrose, 0.3 g/l casamino acid, 2.8 g/l proline, 2 mg/l 2,4-D, 4 g/l gel rite, pH5.8), and incubated for 5 days at 27° C. to 32° C. During this period of time, the seeds were germinated.

(Plant Expression Vector)

*Agrobacterium* EHA101 was transformed with pBI101-Hm3 as prepared above (Hood et al., J. Bacteriol., 168: 1291–1301(1986)). EHA101 is a bacterium in which the vir region of a helper plasmid is derived from potent pathogenic *Agrobacterium* A281. The *Agrobacterium* was cultured in AB medium supplemented with hygromycin (50 mg/l) (glucose (5 g/L), $K_2HPO_4$ (3 g/L), $NaH_2PO_4.2H_2O$ (1.3 g/L), $NH_4Cl$ (1 g/L), KCI (150 mg/L), $CaCl_2.2H_2O$ (10 mg/L), $F_2SO_4.7H_2O$ (2.5 mg/L), pH 7.2, bacto agar (1.5%)(3 g/200 ml), 1M $MgSO_4.7H_2O$ (120 µl/100 ml)) for 2 to 3 days at 25° C. in the dark.

(Infection with *Agrobacterium*)

The transformed *Agrobacterium* was suspended in AAM medium (AA-1 (×1000) 1 ml ($MnSO_4.4-6H_2O$ (1000 mg/100 ml), $H_3BO_3$ (300 mg/100 ml), $ZnSO_4.7H_2O$ (200 mg/100 ml), $Na_2MoO_4.2H_2O$ (25 mg/100 ml), $CuSO_4.5H_2O$ (2.5 mg/100 ml), $CoCl_2.6H_2O$ (2.5 mg/100 ml), KI (75 mg/100 ml)), AA-2 (×1000) 1 ml ($CaCl_2.2H_2O$ (15.0 g/100 ml)), AA-3 (×1000) 1 ml ($MgSO_4.7H_2O$ (25 g/100 ml)), AA-4 (×1000) 1 ml (Fe-EDTA (4.0 g/100 ml)), AA-5(× 1000) 1 ml ($NaH_2PO_4.2H_2O$ (15.0 g/100 ml)), AA-6 (×200) 5 ml (nicotinic acid (20 mg/100 ml), thiamine HCl (200 mg/100 ml), pyridoxine HCl (20 mg/ ml), myo-inositol (2000 mg/100 ml)), AA-Sol (×100) 10 ml (L-arginine (5300 mg/300 ml), glycine (225 mg/300 ml)), AA-KCl (×50) 20 ml (KCl (3 g/20 ml)), casamino acid (500 mg/L), sucrose (68.5 g/L), glucose (36 g/L), L-glutamine (900 mg/L), L-aspartic acid (300 mg/L), pH 5.2) supplemented with 2 µg/ml acetosyringone. The above-described precultured seeds were immersed in this suspension for 90 seconds, and thereafter, transferred to 2N6-AS medium (30 g/l sucrose, 10 g/l glucose, 0.3 g/l casamino acid, 2 mg/l2,4-D, 10 mg/l acetosyringone, 4 g/l gel rite, pH 5.2). Coculture was conducted in the dark for 3 days while incubating at 25° C.

(Removal of Bacteria and Screening)

After completion of coculture, the *Agrobacterium* was removed from the seeds by washing with N6D medium containing 500 mg/l carbenicillin. Thereafter, screening for transformed seeds was conducted under the following conditions.

First screening: the seeds were placed on N6D medium containing 2 mg/l 2,4-D, supplemented with carbenicillin (500 mg/l) and hygromycin (50 mg/l), and incubated at 30° C. for 7 days.

Second screening: the seeds were placed on N6D medium containing 2–4 mg/l 2,4-D, supplemented with carbenicillin (500 mg/l) and hygromycin (50 mg/l), and incubated at 30° C. for additional 7 days.

(Redifferentiation)

Selected transformed seeds were redifferentiated under the following conditions.

First redifferentiation: the selected seeds were placed on redifferentiation medium (MS medium (30 g/l sucrose, 30 g/l sorbitol, 2 g/l casamino acid, 2 mg/l kinetin, 0.002 mg/l NAA, 4 g/l gel rite, pH 5.8) supplemented with carbenicillin (500 mg/l) and hygromycin (25 mg/l)) at 30° C. for two weeks.

Second redifferentiation: the seeds were incubated at 30° C. for additional two weeks in redifferentiation medium identical to that which was used in the first redifferentiation.

(Potting)

The redifferentiated transformant was transferred to rooting medium (hormone-free MS medium supplemented with hygromycin (25 mg/l)). After the growth of roots was confirmed, the transformant was potted.

4. Tissue Specific Expression Observed by GUS Staining

Figure 3:
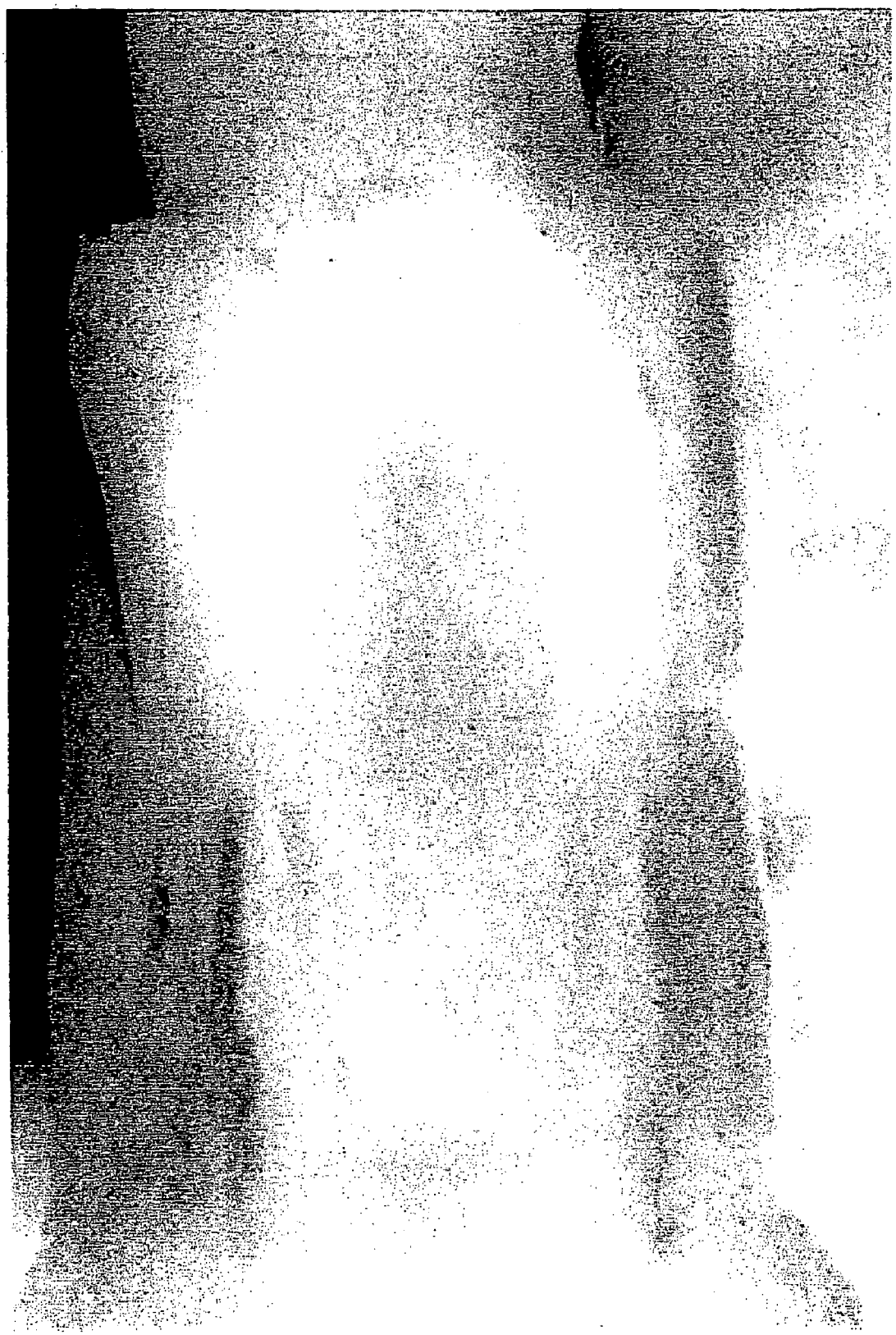
FIG. 3 is a photograph showing a result of GUS histological staining of stems.

Histochemical analysis of GUS activity was conducted in order to study gene expression by the above-described promoter in plant tissue. Such histochemical analysis was conducted by a procedure described in Syokubutsu-saibo-kogaku [Plant Cell Engineering], Vol. 4, No. 4, pp. 281–286. This method is based on Jefferson et al. (EMBO J 6:3901–3907(1987)) with improvements of Kosugi et al., Plant Science 70:133–140(1990). Briefly, an excised section was embedded in 5% (w/w) agar, and the agar block was sliced using a microslicer. Tissue slices having a thickness of 100 to 130 µm were immersed in histochemical substrate solution containing 1 mM 5-bromo-4-chloro-3-indolyl-β-D-glucuronide (X-Gluc), 7% (v/v) methanol, and 50 mM sodium phosphate buffer solution (pH 7.0), and incubated at 37° C. for 4 hours. 2 mM DTT was added immediately after sectioning; in the stage of embedding the section in agar; in the stage of slicing the section; or in the stage of deaerating the section under reduced pressure. 5 mM DTT was added in a GUS reaction at 37° C. Thereafter, the reaction was arrested by addition of ethanol, followed by decoloration. The slice was observed under a microscope. As a result, a high level of GUSactivity was observed in a stem of rice. When the stem was observed by a microscope, the stem wall was stained blue due to the GUS activity (FIG. 3).

Example 2

Expression of the 2β Hydroxylase Gene by the Rice OsGA3ox2 Promoter

Rice seeds were transformed and regenerated to produce transgenic plants in the same manner as that of Example 1, except that in Section 2 of Example 1, instead of the region from the BamHI site to the SmaI site of the rice OsGA3ox2 gene, a region from a XbaI site to a SmaI site of the rice OsGA3ox2 gene was used as a rice OsGA3ox2 gene promoter region (see FIGS. 2A to 2C), and instead of the GUS coding region, the coding region of a gene (OsGA2ox1) encoding 2β hydroxylase was used.

Production of a plant expression vector will be described below.

In order to amplify genomic DNA derived from rice (Oryza sative L., cultivar: Nipponbare), two degenerate oligonucleotide primers (a forward primer: 5'-GGNTTYG-GNGARCAYWCNGAYCC-3' (SEQ ID NO. 4); and a reverse primer5'-GGISHISCRAARTADATIRTISWIA-3' (SEQ ID NO. 5))were designed from conservative regions of a putative *Arabidopsis* GA 2β-hydroxylase gene, dioxygenase *Marah macrocarpa* mRNA (Accession No. Y09113; MacMillan, Plant Physiol. 113, 1369–1377(1997)), rice GA20 oxidase gene (Accession No. U50333; Toyomasu et al., Physiol. Plant. 99, 111–118(1997)), the rice GA 3β hydroxylase gene and other 2-oxoglutaric acid dependent dioxygenase enzymes. Amplified fragments (about 80 bp) were cloned in pCRII (Invitrogen, Carlsbad, Calif.), and were sequenced. One of 64 independent clones contained a novel 2-oxoglutaric acid dependent-like amino acid and was inferred to encode a rice GA 2β hydroxylase gene. DDBJ Nucleotide Sequence Database was searched using the partial amino acid sequence to obtain a rice EST clone (Accession No. C72618). Oligonucleotide primers (a forward primer: 5'-GCGGCGTTCTTCGCG-3' (SEQ ID NO. 6); and a reverse primer: 5'-CTATTGTGAATGAGTACATT-3' (SEQ ID NO. 7)) based on the sequence of the EST clone, and were used as a template for rice genomic DNA in PCR. The amplified fragment was cloned in pCR II (Invitrogen, Carlsbad, Calif.), and were sequenced. The 230 bp fragment was used as a probe for screening of cDNA clones and genome clones.

A cDNA library constructed from immature rice seeds and a genomic library constructed from rice genomic DNA partially digested with Sau3AI were subjected to screening using the probe prepared as described above. Hybridization was conducted at 65° C. for 14 hours in 5×SSC (1×SSC: 0.15 M NaCl, 15 mM sodium citrate), 5× Denhardt's solution (1×Denhardt's solution: 0.02% Ficoll, 0.02% PVP (polyvinylpyrrolidone), 0.02% BSA (bovine serum albumin)), 0.5% (w/v) SDS, and 20 mg/l salmon sperm DNA. Thereafter, a filter was washed in 2×SSC, 0.1% (w/v) SDS, at room temperature. cDNA obtained by the screening is referred to as OsGA2ox1, which contained a 1,146 bp open reading frame containing a sequence of 382 amino acids (data not shown). A 5' terminal portion of OsGA2ox1 cDNA was excised with a restriction enzyme EcoRI, while a 3' portion thereof was excised with a restriction enzyme EcoRV. The resultant cDNA was blunt ended so as to be linked in frame to a pBI101 vector. Thereafter, this vector was linked to a SmaI site. The XbaI-HindIII fragment of the rice OsGA3ox2 gene obtained in Section 2 of Example 1 was further digested with XbaI and SmaI. In the pBI101 vector, the OsGA3ox2 fragment was linked to a XbaI-SmaI site upstream of OsGA2ox1.

Figure 4:
FIG. 4 is a photograph showing a dwarf plant which was transformed with an OsGA2ox1 gene linked with a promoter of the present invention.

Grown plants are shown in FIG. 4. A plant obtained from a transformed seed is shown to the right of FIG. 4, while a control plant (untreated) is shown to the left of FIG. 4 (Nipponbare). The transformed plant clearly had a short height and was dwarf as compared to the control plant. This indicates that 2β hydroxylase was expressed in the stem by the promoter of the present invention.

INDUSTRIAL APPLICABILITY

The OsGA3ox2 gene promoter of the present invention has a considerably high level of activity in stems and leaves. Therefore, the present invention is useful for breeding of plants, such as rice and the like, by gene manipulation of vegetative growth tissue.

The invention claimed is:

1. An isolated DNA having promoter activity for expressing an exogenous gene specifically in plant vegetative growth tissue,
   wherein the DNA has the sequence of nucleic acids 384 to 2406 as set forth in SEQ ID NO. 1, whose promoter activity is equivalent to that of the sequence set forth as SEQ ID NO. 1.

2. An expression vector, comprising DNA according to claim 1 and an exogenous gene expressibly linked to the DNA.

3. The expression vector according to claim 2, wherein the exogenous gene has a function of suppressing elongation of stems and/or leaves.

4. The expression vector according to claim 2, wherein the exogenous gene is a gene encoding 2β hydroxylase.

5. A plant cell, transformed with the expression vector according to claim 2.

6. The plant cell according to claim 5, wherein the plant cell is a monocotyledonous plant cell.

7. The plant cell according to claim 5, wherein the plant cell is a dicotyledonous plant cell.

8. A plant, regenerated from the plant cell according to claim 5.

9. A progeny of the plant according to claim 8, wherein the progeny comprises the expression vector.

10. A propagator of the plant according to claim 8, wherein said propagator is pollen.

11. A seed, obtained from the progeny according to claim 9, wherein the seed comprises the expression vector.

12. A method for introducing an exogenous gene into plants, wherein the exogenous gene is intended to be expressed specifically in plant vegetative growth tissue, the method comprising the steps of: transforming a plant cell with the expression vector according to claim 2; and obtaining a plant by redifferentiation of the transformed plant cell.

13. The method according to claim 12, wherein the exogenous gene has a function of suppressing elongation of stems and/or leaves.

14. The method according to claim 12, wherein the plant cell is a monocotyledonous plant cell.

15. The method according to claim 12, wherein the plant cell is a dicotyledonous plant cell.

* * * * *

SEQUENCE LISTING

<160> NUMBER OF SEQ ID NOS: 7

<210> SEQ ID NO 1
<211> LENGTH: 2406
<212> TYPE: DNA
<213> ORGANISM: Oryza sativa
<220> FEATURE:
<221> NAME/KEY: exon
<222> LOCATION: (1567)..(2039)
<220> FEATURE:
<221> NAME/KEY: exon
<222> LOCATION: (2151)..(2406)

<400> SEQUENCE: 1

| | |
|---|---|
| ggatcccacc caatggcgac gcgccctctg ctccatcgat cccgacaacg catccagaag | 60 |
| gcgccggcga cacctcgccg ccgatcgtcc gccgcccta gtcgccgcca tctctcgatc | 120 |
| atcccctgt cccttccctt ccacgcacgg ccggccattc catcgccgcc tacctccaga | 180 |
| cccaatgcat cctctctctc tctctctctc tctctctctc tctctctctc | 240 |
| tctctctctc tctctctctc tgttaatttt gtaatgtatt agcaaccatt catggatgga | 300 |
| tggatgatga tgatcatggc ctctgtcctc tgtttttact cgtggctgca gactagtgct | 360 |
| gtcttttctc ttgtttgctg ttctagaatc tgtgtgctgt tttctaaaca aattactgtt | 420 |
| tatatttgtt ttgttttgtt tattttgta gttgtaatat aaggttagtc ttcttagtaa | 480 |
| atatattgaa aaagaagaa gtagataaca cggtttgaat cttggtaatt gtaccgtgct | 540 |
| cgacaaatta ggacgtaatc ctttcgtttc agattataaa atattttgac tttagtcaaa | 600 |
| gtcatgttgt ttcaagtttg actaatttta tagataaata taataatatt tataatatta | 660 |
| aattagttaa ttaaatatat tttcataata aatttgtctt gagttaaaaa tattactact | 720 |
| ttttctataa aattggtcaa acttaaagca gtttgattt gactaaagtc aaaacgtctt | 780 |
| ataacctgaa acggatgtag tactgtatat gggaactagc atgaagatct tgctactgaa | 840 |
| agtaaaatat cgaatgaaat tcgacgtgta tgagaattat acggtaatca taattaatta | 900 |
| gaagtggctg catgtgagaa tatttggttc taaagcagac agacgaatta aaaaaaaaca | 960 |
| ccacggcaac ggaggacgct actgttcctg tgaaattcct atgtttaatt acctaatctg | 1020 |
| ttttattgta atgtgataat taaaaattac tctggtgctt atttcacatt gtgattttac | 1080 |
| tttactataa cataacttaa tttgtatgaa tatgtgtgtt tattaattgg gtggcagtgc | 1140 |
| cactagccag ccagggagtg gtgatgagca tactagctag atttgtgttg tgtagctaag | 1200 |
| ctggtggcct tgtgtgctcc acatcactcc aaaccctctg tcccaatcac cacattttt | 1260 |
| cctctccaaa tctattaatt aatgatccat ttcaattctt catcactgat ttattcacca | 1320 |
| attaattctc tctttttttt ttcttccact acgctccaaa acttctctcc ctatatatac | 1380 |
| ctctcccttg tacttgtcca gttcttacac tcgtctcact ttactactca ttccactatt | 1440 |
| gtaaagtcat agaaaaaatt tatatagaga gaaaaaatta gtgtttgtta ttgttactgg | 1500 |
| ctttctgcca gacgagacga gcgagcgcgc gagtgtgttg ctctggtcat ctcgtcgtcg | 1560 |

| tcggcg | atg | ccg | acg | ccg | tcg | cac | ttg | aag | aac | ccg | ctc | tgc | ttc | gac | 1608 |
|---|---|---|---|---|---|---|---|---|---|---|---|---|---|---|---|
| | Met | Pro | Thr | Pro | Ser | His | Leu | Lys | Asn | Pro | Leu | Cys | Phe | Asp | |
| | 1 | | | 5 | | | | | 10 | | | | | | |

| ttc | cgg | gcg | gcg | agg | cgg | gtg | ccg | gag | acg | cac | gcg | tgg | ccg | ggg | ctg | 1656 |
|---|---|---|---|---|---|---|---|---|---|---|---|---|---|---|---|---|
| Phe | Arg | Ala | Ala | Arg | Arg | Val | Pro | Glu | Thr | His | Ala | Trp | Pro | Gly | Leu | |
| 15 | | | | 20 | | | | | 25 | | | | | 30 | | |

| gac gac cac ccg gtg gtg gac ggc ggc ggc ggc ggc gag gac gcg | 1704 |

```
Asp Asp His Pro Val Val Asp Gly Gly Gly Gly Gly Glu Asp Ala
            35                  40                  45 gtg ccg gtg gtg gac gtc agg gcg ggc gac gcg gcg gcg cgg gtg gcg   1752
Val Pro Val Val Asp Val Arg Ala Gly Asp Ala Ala Ala Arg Val Ala
            50                  55                  60 cgg gcg gcg gag cag tgg ggc gcg ttc ctt ctg gtc ggg cac ggc gtg   1800
Arg Ala Ala Glu Gln Trp Gly Ala Phe Leu Leu Val Gly His Gly Val
            65                  70                  75 ccg gcg gcg ctg ctg tcg cgc gtc gag gag cgc gtc gcc cgc gtg ttc   1848
Pro Ala Ala Leu Leu Ser Arg Val Glu Glu Arg Val Ala Arg Val Phe
        80                  85                  90 tcc ctg ccg gcg tcg gag aag atg cgc gcc gtc cgc ggc ccc ggc gag   1896
Ser Leu Pro Ala Ser Glu Lys Met Arg Ala Val Arg Gly Pro Gly Glu
95              100                 105                 110 ccc tgc ggc tac ggc tcg ccg ccc atc tcc tcc ttc ttc tcc aag ctc   1944
Pro Cys Gly Tyr Gly Ser Pro Pro Ile Ser Ser Phe Phe Ser Lys Leu
                115                 120                 125 atg tgg tcc gag ggc tac acc ttc tcc cct tcc tcc ctc cgc tcc gag   1992
Met Trp Ser Glu Gly Tyr Thr Phe Ser Pro Ser Ser Leu Arg Ser Glu
            130                 135                 140 ctc cgc cgc ctc tgg ccc aag tcc ggc gac gac tac ctc ctc ttc tg g  2040
Leu Arg Arg Leu Trp Pro Lys Ser Gly Asp Asp Tyr Leu Leu Phe Cys
            145                 150                 155 tatatataca tatatatata ctctcccatg cattccatgc acatacactc tacgtatata  2100
tctacctcta cgtatatatc tacgtattga tctacgtata atatacgcag t gac gtg  2157
                                                       Asp Val
                                                          160 atg gag gag ttt cac aag gag atg cgg cgg cta gcc gac gag ttg ctg   2205
Met Glu Glu Phe His Lys Glu Met Arg Arg Leu Ala Asp Glu Leu Leu
                165                 170                 175 agg ttg ttc ttg agg gcg ctg ggg ctc acc ggc gag gag gtc gcc gga   2253
Arg Leu Phe Leu Arg Ala Leu Gly Leu Thr Gly Glu Glu Val Ala Gly
            180                 185                 190 gtc gag gcg gag agg agg atc ggc gag agg atg acg gcg acg gtg cac   2301
Val Glu Ala Glu Arg Arg Ile Gly Glu Arg Met Thr Ala Thr Val His
        195                 200                 205 ctc aac tgg tac ccg agg tgc ccg gag ccg cgg cga gcg ctg ggg ctc   2349
Leu Asn Trp Tyr Pro Arg Cys Pro Glu Pro Arg Arg Ala Leu Gly Leu
210                 215                 220 atc gcg cac acg gac tcg ggc ttc ttc acc ttc gtg ctc cag agc ctc   2397
Ile Ala His Thr Asp Ser Gly Phe Phe Thr Phe Val Leu Gln Ser Leu
225                 230                 235                 240 gtc ccg ggg                                                       2406
Val Pro Gly <210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: a template
                        and degenerative primer for GA3 beta
                        hydroxylase gene.
<220> FEATURE:
<221> NAME/KEY: misc_feature
<222> LOCATION: 3, 6, 12, 15
<223> OTHER INFORMATION: n= a, t, g, or c

<400> SEQUENCE: 2
gtngtnaarg tnggngarrt                                               20
```

```
<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: a template
                        and degenerative primer for GA3 beta
                        hydroxylase gene.
<220> FEATURE:
<221> NAME/KEY: misc_feature
<222> LOCATION: 15, 18
<223> OTHER INFORMATION: n= a, t, g, or c

<400> SEQUENCE: 3
ayytartcrt tggangtnac                                                   20

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: a forward
                        primer designed based on the conserved regions
                        among genes encoding pathway.
<220> FEATURE:
<221> NAME/KEY: misc_feature
<222> LOCATION: 3, 9, 18
<223> OTHER INFORMATION: n= a, t, g, or c

<400> SEQUENCE: 4
ggnttyggng arcaywcnga ycc                                               23

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: a reverse
                        primer designed based on the conserved regions
                        among genes encoding for enzymes involved in
                        GA biosynthetic pathway.
<220> FEATURE:
<221> NAME/KEY: misc_feature
<222> LOCATION: 3, 6, 18, 21, 24
<223> OTHER INFORMATION: n= a, t, g, or c

<400> SEQUENCE: 5
ggnshnscra artadatnrt nswna                                             25

<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence: a forward
                        primer designed based on the EST clone
                        (Accession No. C72618).

<400> SEQUENCE: 6
gcggcgttct tcgcg                                                        15

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: a reverse
                        primer designed based on the EST clone
                        (Accession No. C72618).
```

-continued

```
<400> SEQUENCE: 7
ctattgtgaa tgagtacatt                                              20
```